United States Patent
Balsells

(10) Patent No.: US 7,274,964 B2
(45) Date of Patent: Sep. 25, 2007

(54) USE OF AN AXIAL CANTED COIL SPRING AS AN ELECTRICAL CONTACT TO MINIMIZE RESISTIVITY VARIATIONS UNDER DYNAMIC LOADS

(75) Inventor: Peter J. Balsells, Newport Beach, CA (US)

(73) Assignee: Bal Seal Engineering Co., Inc., Lake Forest, CA (US)

( * ) Notice: Subject to any disclaimer, the term of this patent is extended or adjusted under 35 U.S.C. 154(b) by 19 days.

(21) Appl. No.: 11/104,798

(22) Filed: Apr. 13, 2005

(65) Prior Publication Data

US 2005/0234521 A1    Oct. 20, 2005

Related U.S. Application Data

(60) Provisional application No. 60/562,939, filed on Apr. 16, 2004.

(51) Int. Cl.
*A61N 1/375* (2006.01)

(52) U.S. Cl. .............................. 607/37; 607/36; 607/38; 439/349; 439/352; 439/840; 439/909; 267/166

(58) Field of Classification Search ............ 607/36–38; 439/909, 840, 349, 352; 267/166
See application file for complete search history.

(56) References Cited

U.S. PATENT DOCUMENTS

| | | | | |
|---|---|---|---|---|
| 4,830,344 A | * | 5/1989 | Balsells ...................... 267/167 |
| 4,934,366 A | * | 6/1990 | Truex et al. ................. 607/37 |
| 5,503,375 A | * | 4/1996 | Balsells ...................... 267/167 |
| 5,545,842 A | * | 8/1996 | Balsells ...................... 174/372 |
| 6,835,084 B2 | | 12/2004 | Poon et al. | |
| 7,055,812 B2 | * | 6/2006 | Balsells ...................... 267/167 |
| 2003/0157846 A1 | * | 8/2003 | Poon et al. ................. 439/840 |

* cited by examiner

*Primary Examiner*—Carl Layno
*Assistant Examiner*—Shevon Johnson
(74) *Attorney, Agent, or Firm*—Walter A. Hackler

(57) ABSTRACT

A medically implantable electrical connector includes a housing having a bore with an internal groove therein along with a pin sized for insertion into the housing bore. A film removing spring is disposed in the housing groove dynamic loading of the spring in the groove by the pin causing scraping of film from the groove and pin surfaces to provide lowered electrical resistance therebetween.

12 Claims, 5 Drawing Sheets

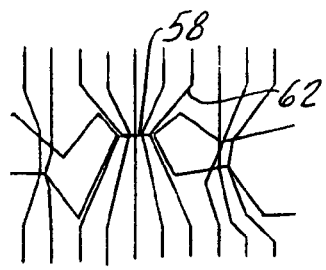
_FIG. 4A._
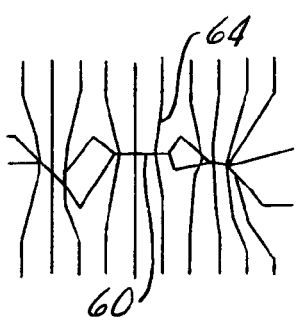
_FIG. 4B._
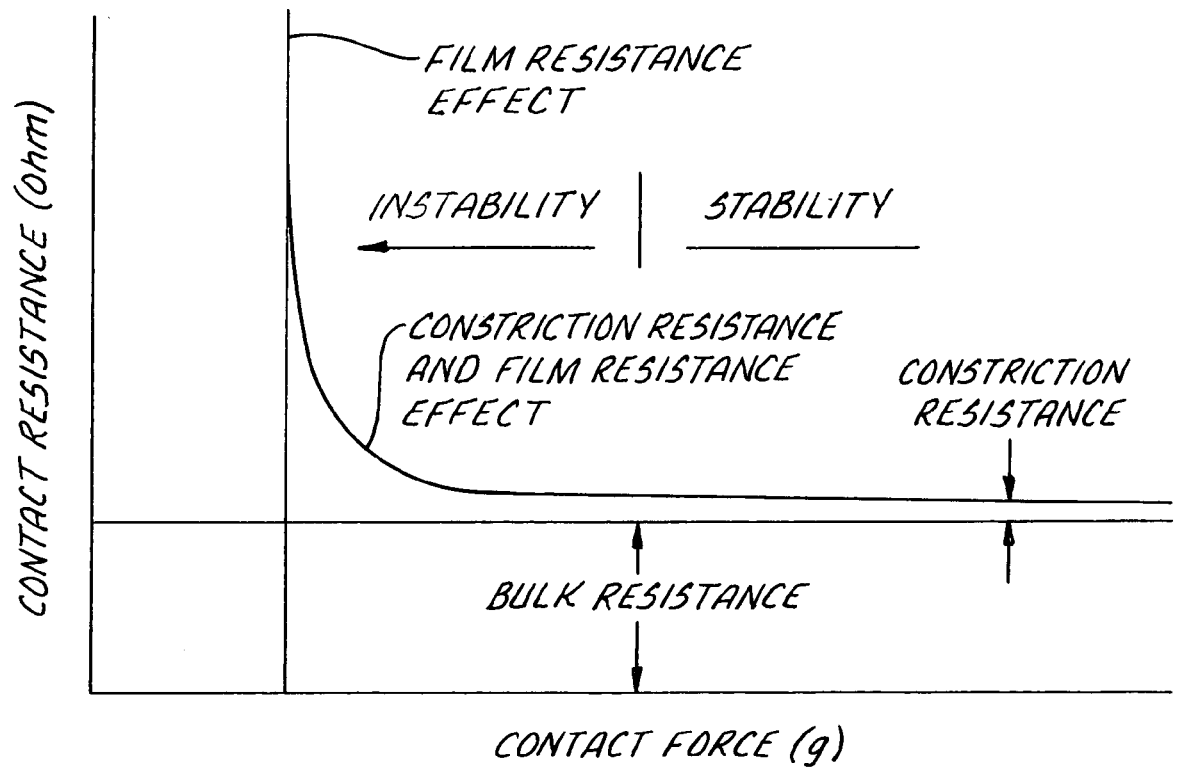
_FIG. 5._

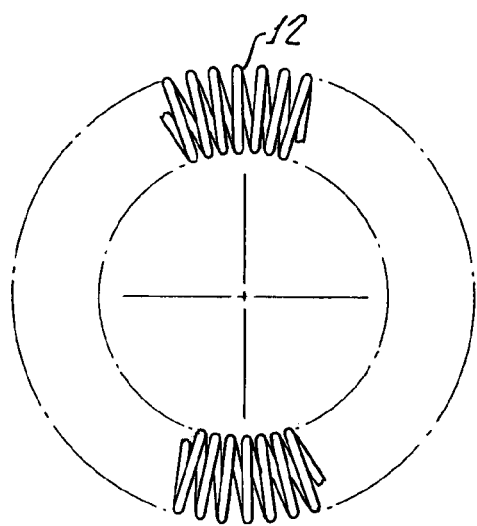
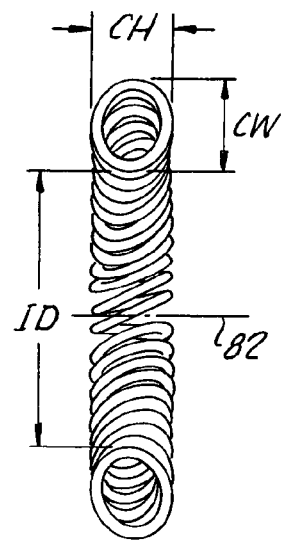
Fig. 6A.  Fig. 6B.
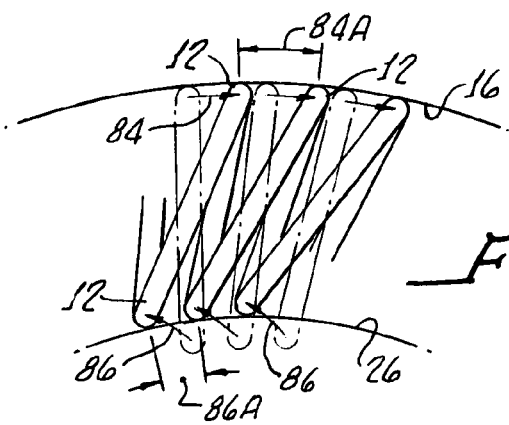
Fig. 7.
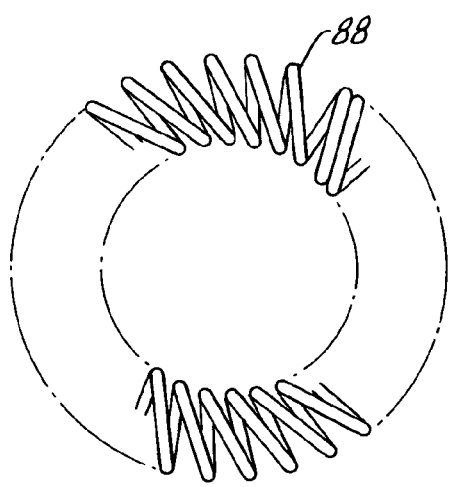
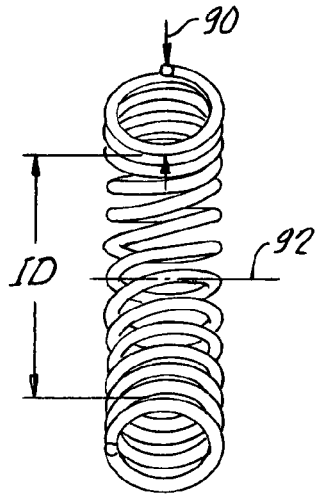
Fig. 8A.  Fig. 8B.

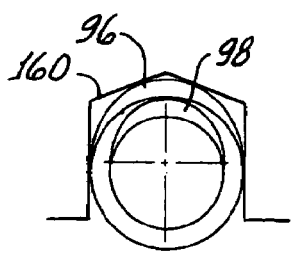
_FIG. 9A._
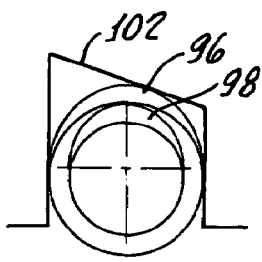
_FIG. 9B._
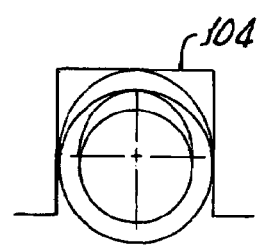
_FIG. 9C._
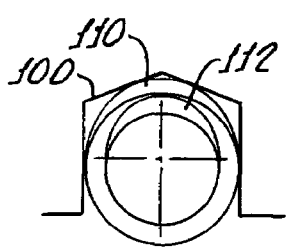
_FIG. 10A._
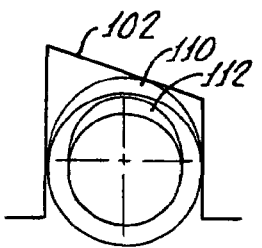
_FIG. 10B._
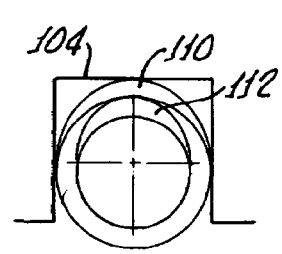
_FIG. 10C._
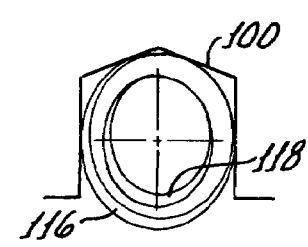
_FIG. 11A._
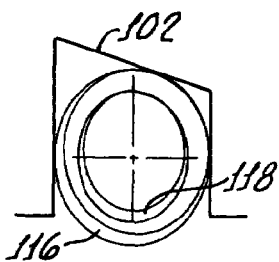
_FIG. 11B._
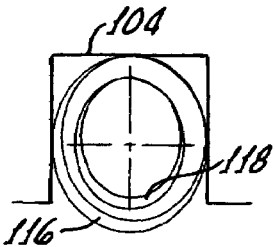
_FIG. 11C._
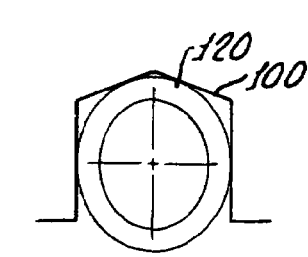
_FIG. 12A._
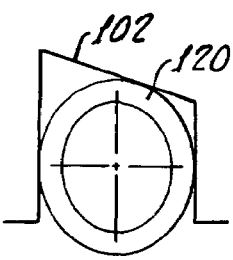
_FIG. 12B._
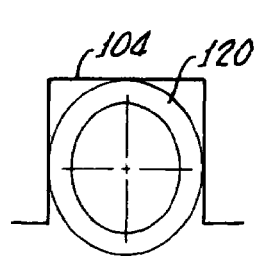
_FIG. 12C._

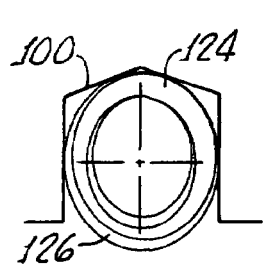
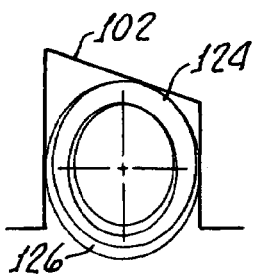
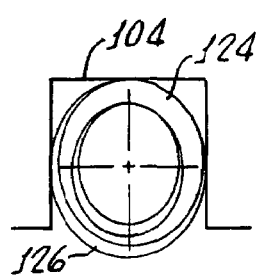
FIG. 13A.   FIG. 13B.   FIG. 13C.
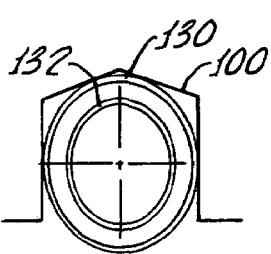
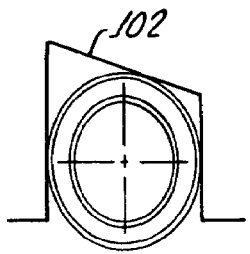
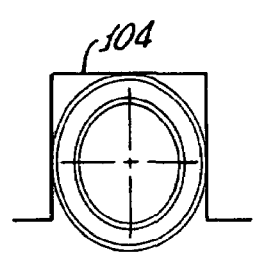
FIG. 14A.   FIG. 14B.   FIG. 14C.
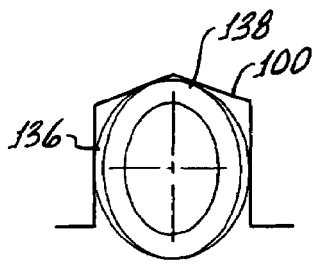
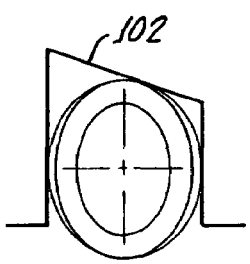
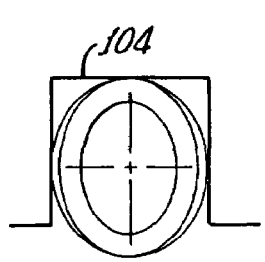
FIG. 15A.   FIG. 15B.   FIG. 15C.
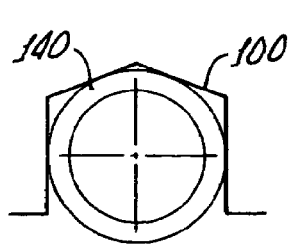
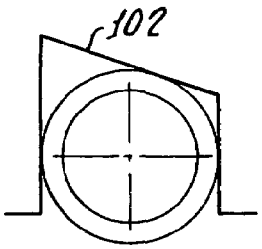
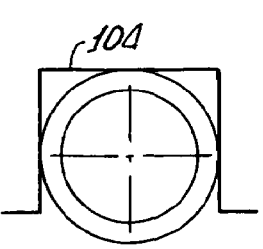
FIG. 16A.   FIG. 16B.   FIG. 16C.

USE OF AN AXIAL CANTED COIL SPRING AS AN ELECTRICAL CONTACT TO MINIMIZE RESISTIVITY VARIATIONS UNDER DYNAMIC LOADS

The present application claims priority from U.S. Provisional Patent Application Ser. No. 60/562,939 filed Apr. 16, 2004, which is to be incorporated herein in its entirety including all specifications and drawings.

The present invention is generally related to electrical connectors and is more particularly directed to medically implantable electrical connectors with minimized variability of resistivity.

Medical connectors are used in a great number of medical devices such as, for example, pace makers, defibulators, neuro stimulators, and the like. Medically implantable electrical connectors are inherently different than most other electrical connectors due to the environment and critical nature of their use.

As set forth in U.S. Pat. No. 6,835,084 to Poon and Balsells, electrical contacts using canted coil springs have significant advantages and compactness and the ability to compensate for eccentricities in the pin and the housing precious metals. This referenced patent is to be incorporated herewith in its entirety by this specific reference thereto. The object of the hereinabove referenced U.S. Patent is to reduce resistivity and resistivity variability under static and dynamic loading utilizing combinations of medically implantable material.

The present invention provides for the minimization of variability of resistivity of an electrical contact through the use of spring selection and dynamic loading.

SUMMARY OF THE INVENTION

A medically implantable electrical connector in accordance with the present invention generally includes a housing having a bore therethrough with an internal groove therein along with a pin sized for insertion into the housing bore.

A film removing spring is disposed in the housing groove and dynamic loading of the spring in the groove by the pin causes scraping of the film (typically an oxide) from the groove and pin surfaces to provide both lowered and consistent electrical resistance therebetween. That is, not only is there a reduction in resistance but also a reduction in resistance variability.

It has been found that this feature is only available through the use of axial canted coil springs, as opposed to, for example, radial canted coil springs. The orientation of the coils in an axial canted coil spring under dynamic loading rub, or scrape, electrically resistant film, thus providing stable contact between housing-spring-pin surfaces.

In one embodiment of the present invention, the film removing spring includes both axial, elliptical, and axial round coils with the elliptical and round coils being offset radially from one another. In this embodiment, a coil height of the elliptical coils may be greater than the coil height of the round coils. Alternatively, the height of the round coils may be greater than the coil height of the elliptical coils.

In another embodiment of the present invention, the film removing spring includes elliptical coils of different coil heights and more specifically the coils of different coil heights may be offset radially and axially from one another. In addition, the coils of different coil height may be offset radially from one another.

In yet another embodiment of the present invention, the film removing spring may comprise round coils and in all of the hereinabove recited embodiments, the pin may include an external groove for capturing the spring in order to removably latch the spring within the housing bore.

The features of the present invention, namely a minimized variation and resistivity by the utilization of axial canted coil springs may be effected through housing grooves having a V-bottom, a flat bottom, or a tapered bottom.

BRIEF DESCRIPTION OF THE DRAWINGS

The present invention will be better understood by referenced to the accompanying drawings, in which:

FIG. 4 illustrates the effect of increased force on the constriction and film resistance;

FIG. 5 shows a relationship between contact force and contact resistance;

FIGS. 6a and 6b illustrate the characteristic structure of an axial canted coil spring;

FIG. 7 illustrates scraping action provided by the use of an axial coil spring;

FIGS. 8a and 8b illustrate the structural characteristics of a radial canted coil spring shown for comparison purposes with the axial canted coil spring shown in FIGS. 6a, 6b; and FIGS. 9a, 9b, 9c, 10a, 10b, 10c, 11a, 11b, 11c, 12a, 12b, 12c, 13a, 13b, 13c, 14a, 14b, 14c, 15a, 15b, 15c, and 16a, 16b, 16c illustrate various embodiments in accordance with the present invention.

DETAILED DESCRIPTION

Figure 1:
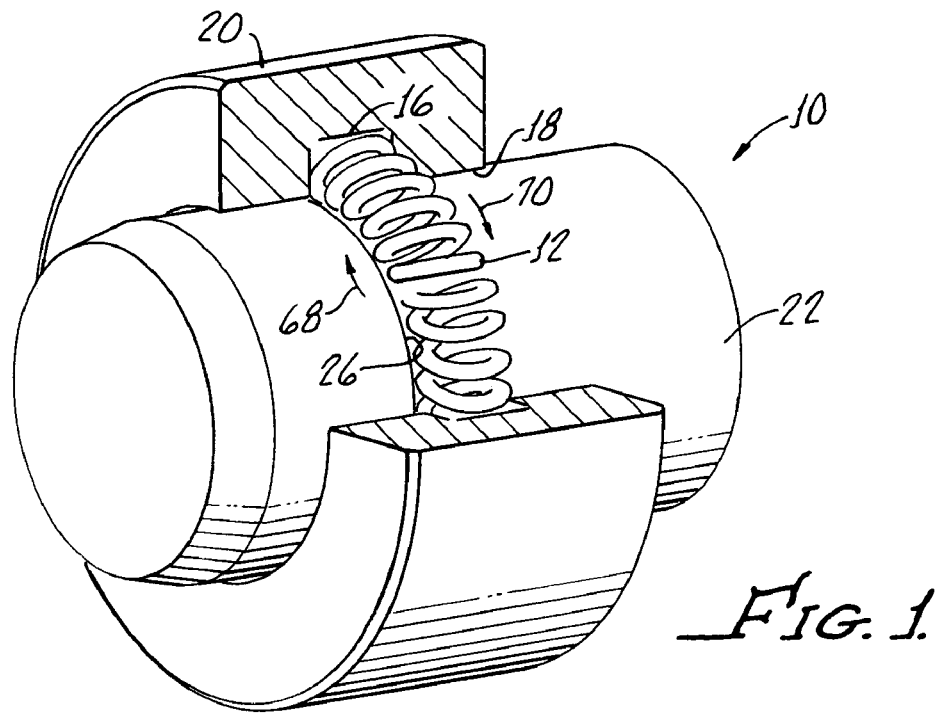
FIG. 1 is a perspective view of an electrical contact, or connector, utilizing an axial canted coil spring.

With reference to FIG. 1, there is shown an electrical contact, or connector, 10 in accordance with the present invention utilizing an axial canted coil spring 12, as will be hereinafter described and defined in greater detail, disposed in an internal groove 16 of a bore 18 through a housing 20. A pin 22 is sized for insertion and to the housing bore 18 and may include an external groove 26 for capturing the spring 12 in order to removably latch the spring 12 and pin 22 within the housing 20.

The spring 12 functions to remove film, not shown in FIG. 1, on the housing groove 16 and pin groove 26 through dynamic loading of the axial canted coil spring 12 in the groove 16 which causes scraping of the film from the groove 16, 26 to provide lowered electrical resistance therebetween.

Figure 2:
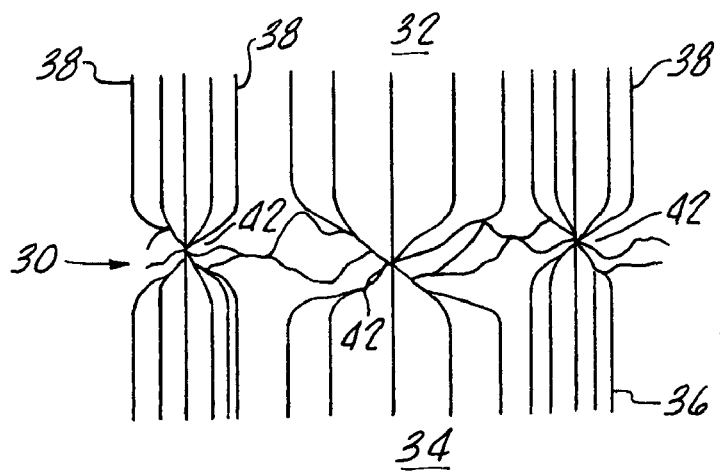
FIG. 2 is a plot of current flow across an interface between two different surfaces illustrating bulk resistance is due in part from constriction resistance at contacts between surface asperities. The current flow pattern changes to flow through the contact points, which is influenced by the total number of contacts. Bulk resistance also includes film resistance which results from the formation of film, such as an oxide, on the contact surface.

The housing 20, spring 12, and pin 22 may be formed from any suitable medically implantable material. To further understand the present invention, a brief description of bulk resistance across an interface 30 between two surfaces 32, 34, as shown in FIG. 2 is in order.

Current flow 36, as indicated by arrows 38 across the interface 30 between the surfaces 32, 34 is subject to constriction resistance which results from contact between surface asperities.

The current flow pattern changes to flow through contact points 42 and is, of course, influenced by the total number of contact points 42.

Figure 3:
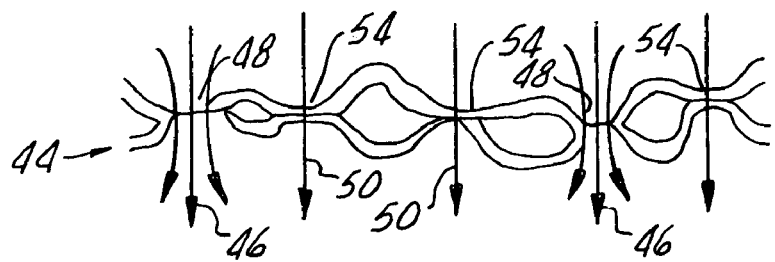
FIG. 3 further illustrates constriction and film resistance.

Film resistance results from the formation of film on the surfaces at an interface 44 as is illustrated in FIG. 3 which illustrates current flow indicated by arrows 46 through contact points 48 as well as current flow indicated by the arrows 50 through films 54.

Thus, resistivity and current flow are the result of combined constriction resistance and film resistance.

Increased force also has an effect on constriction and film resistance, as illustrated in FIGS. 4a, 4b. With low contact force, FIG. 4A, contact points 58 are smaller in cross section than contact points 60 under high contact force, as illustrated in FIG. 4b. Corresponding current flow lines 62, 64 are also shown in FIGS. 4a and 4b to illustrate the effective increased force on resistance.

A certain amount of normal force at the contact area 62 is require to break through the film. As the contact forces increased, the Hertz stress (a highly localized stress) increases. This effect results in increasing contact surface area 60, thus reducing both constriction resistance and the film resistance. It is clear that the lowest resistance and variability of that resistance is achieved by providing a very high normal force.

However, a low normal force is required in many applications. For example, to avoid damage to a lead wire, a physician uses minimal force to insert the pin 22 into the housing 20 in a medical electronic device with multiple contacts, only when contact being shown in FIG. 1 for clarity. Other applications utilizing the low normal force are those that require a high number of cycles where frictional wire is important.

FIG. 5 shows the relationship between contact force and contact resistance. There is a region of instability where a variation force will result in a variation of resistivity. Extensive testing is demonstrated that the variability and resistivity in this region is reduced by a factor of 20 or more through the use of an axial canted coil spring constraint and the housing as opposed to other types of springs, for example, a radial canted coil spring.

The use of an axial canted coil spring provides for rotation of the spring under load, as indicated by the arrows 68, 70 in FIG. 1 as dynamic forces are applied through the insertion of the pin into the housing 20, the axial canted coil spring reacts to the forces to maintain a normal contact force high enough to penetrate a film as well as providing the scraping action that removes the surface film as it compresses along an axis 74 of the spring 12 under compression loading shown by arrows 76 in FIGS. 6a, 6b. This service film is typically an oxide.

As shown in FIGS. 6a and 6b, an axial canted coil spring yields to compression force arrow 80, which is generally in a direction parallel to a centerline 82 of the spring 12. Thus, when compressed radially as illustrated in FIG. 1, coil movement occurs, indicated by arrows 84, 86 in FIG. 7, and results in scraping or rubbing film removing action.

By way of comparison only, a radial canted coil spring 88 illustrated in FIG. 8a, 8b compresses under compression force, see arrow 90, which is perpendicular to its centerline 92. Thus, a little coil movement occurs during this coil compression and such a radial canted coil spring 88 does not function in any scraping action for film removal.

Thus, it has been unexpectedly found that use of an axial spring under dynamic load decreases the resistance of the connector 10 compared to an increase of resistance with the use of a radiant spring under dynamic load. Table 1 shows the results of measurement of an axial spring and a radial spring connectors under static load and Table 2 shows the results of measurements of an axial spring and a radial spring connectors under dynamic load.

Tables 1 and 2 show that in the case of the radial spring, the average resistance increased by 514% when going from a static condition to a dynamic one. For the axial spring, the average resistance decreased by 35%.

| | |
|---|---|
| Average radial static resistance | .0105 ohms |
| Average radial dynamic resistance | .054 ohms |
| percent increase | 514% |
| Average axial static resistance | .067 ohms |
| Average axial dynamic resistance | .0437 |
| percent decrease | 35% |

Further enhancement of this film removing enhancement by coil movement is effected through the use of multiple springs with multiple coil shapes, such as, for example, combination of an axial elliptical coil 96 and an axial round coil 98, as illustrated in FIGS. 9a, 9b, and 9c for grooves 100 V-bottom, tapered bottoms, and flat bottoms respectively.

In this embodiment, the coil height (CH) of the axial elliptical coil 96 is equal to the coil height (CH) of the axial round coil 98 while the coil width (CW) of the axial elliptical coil 96 is greater than the coil width (CW) of the axial round coil 98. In addition, as shown in FIGS. 9a, 9b, and 9c, the axial round coil 98 is offset from the axial elliptical coil 96 while the inside diameters for both the coils 96, 98 is the same.

Another embodiment of the present invention, is illustrated in FIGS. 10a, 10b, 10c which common reference characters represents identical or substantial similar element. In this embodiment, an axial elliptical coil 110 and an axial round coil 112 are utilized with the coil height of the axial elliptical coil 110 being greater than the coil height of the axial round coil 112 while the coil width of the axial elliptical coil 110 is greater than the coil width of the axial round coil 112. In this embodiment shown in the V-bottom 100, the tapered bottom 102, and the flat bottom 104 grooves. The axial round coil 112 is offset from the axial elliptical coil 110 and the inside diameters for both the coils 110, 112 are the same.

A further embodiment of the present invention is illustrated in FIGS. 11a, 11b, 11c for V-bottom, tapered bottom, and flat bottom grooves 100, 102, 104 utilizing first and second axial elliptical coils 116, 118 in which the coil height of the first axial elliptical coil 116 is greater than the coil height of the second axial elliptical coil 118, the coil width of the first axial elliptical coil 116 is greater than the coil width at the second axial elliptical coil 118, the second elliptical coil 118 is offset from the first elliptical coil 116 and the outside diameters of the coils 116, 118 are the same for both the first and second elliptical coils 116, 118.

Still another embodiment of the present invention is illustrated in FIGS. 12a, 12b, 12c, again for V-bottom, tapered bottom, and flat bottom grooves 100, 102, 104 in which a first elliptical coil 120 and a second elliptical coil, hidden from view, have equal coil heights and coil widths There is no offset between the first elliptical coil and the second elliptical coil and the coils have identical inside and outside diameters.

In another embodiment of the present invention, as illustrated in FIGS. 13a, 13b, 13c again for V-bottom, tapered bottom, and flat bottom grooves 100, 102, 104, in which a first axial elliptical coil 124 and a second axial elliptical coil 126 have the same outside diameter. However, the coil height of the second elliptical coil 126 is greater than the coil height of the first elliptical coil 124, the coil width of the second elliptical coil 126 is greater than the coil width of the first elliptical coil 124 and the second elliptical coil 126 is offset from the first elliptical coil 124, radially.

Still yet another embodiment of the present invention is illustrated in FIGS. 14a, 14b, 14c for V-bottom, tapered bottom, and flat bottom grooves 100, 102, 104, illustrating a first axial elliptical coil 130 and a second axial elliptical coil 132 with the coil height of the second axial elliptical coil 132 is greater than the coil height of the first elliptical coil 130 and the coil width of the second elliptical coil 132 is greater than the coil width of the first elliptical coil 130. In this embodiment, there is no offset between the elliptical coils 130, 132 and both coils 130, 132 have the same center.

Another embodiment of the present invention is illustrated in FIGS. 15a, 15b, 15c for V-bottom, tapered bottom, and flat bottom grooves 100, 102, 104 in which a first axial elliptical coil 136 has a coil height greater than the coil height of the second elliptical coil 138 while the coil width of both elliptical coils 136, 138 are equal. In this embodiment, there is no offset between the coils 136, 138 and both coils 136, 138 have the same center.

A final embodiment of the of the present invention is illustrated in FIGS. 16a, 16b, 16c again for V-bottom, tapered bottom, and flat bottom grooves 100, 102, 104 in which there is an axial round coil 140 and a second axial round coil, hidden, since the coil widths and coil heights are equal and there is no offset.

A large number of embodiments illustrated operate in the same principle in providing a film removing spring with a various coils disposed in different shaped grooves 100, 102, 104.

Although there has been hereinabove described a specific use of an axial canted coil spring as an electrical contact to minimize resistivity variations under dynamic loads in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

TABLE 1

AXIAL AND RADIAL STATIC REFERENCES

|  | Research Report Number | Contact Part Number | Contact Item Number | Pin Part Number | Pin Item Code | Test Item | Header position | Filename |
|---|---|---|---|---|---|---|---|---|
| Axial Static | 213-28 | X212669 | Axial | .053 OD | NA | 1 | 1 | AR_213-28_Axial_X212669_1_1.txt |
|  | 213-28 | X212669 | Axial | .053 OD | NA | 1 | 1 | AR_213-28_Axial_X212669_1_2.txt |
|  | 213-28 | X212669 | Axial | .053 OD | NA | 1 | 1 | AR_213-28_Axial_X212669_1_3.txt |
|  | 213-28 | X212669 | Axial | .053 OD | NA | 1 | 1 | AR_213-28_Axial_X212669_1_4.txt |
|  | 213-28 | X212669 | Axial | .053 OD | NA | 1 | 1 | AR_213-28_Axial_X212669_1_5.txt |
|  | 213-28 | X212669 | Axial | .053 OD | NA | 1 | 1 | AR_213-28_Axial_X212669_1_6.txt |
|  | 213-28 | X212669 | Axial | .053 OD | NA | 1 | 1 | AR_213-28_Axial_X212669_1_7.txt |
|  | 213-28 | X212669 | Axial | .053 OD | NA | 1 | 1 | AR_213-28_Axial_X212669_1_8.txt |
|  | 213-28 | X212669 | Axial | .053 OD | NA | 1 | 1 | AR_213-28_Axial_X212669_1_9.txt |
|  | 213-28 | X212669 | Axial | .053 OD | NA | 1 | 1 | AR_213-28_Axial_X212669_1_10.txt |
|  | 213-28 | X212669 | Axial | .053 OD | NA | 1 | 1 | AR_213-28_Axial_X212669_1_11.txt |
|  | 213-28 | X212669 | Axial | .053 OD | NA | 1 | 1 | AR_213-28_Axial_X212669_1_12.txt |
|  | 213-28 | X212669 | Axial | .053 OD | NA | 1 | 1 | AR_213-28_Axial_X212669_1_13.txt |
|  | 213-28 | X212669 | Axial | .053 OD | NA | 1 | 1 | AR_213-28_Axial_X212669_1_14.txt |
|  | 213-28 | X212669 | Axial | .053 OD | NA | 1 | 1 | AR_213-28_Axial_X212669_1_15.txt |
|  | 213-28 | X212669 | Axial | .053 OD | NA | 1 | 1 | AR_213-28_Axial_X212669_1_16.txt |
|  | 213-28 | X212669 | Axial | .053 OD | NA | 1 | 1 | AR_213-28_Axial_X212669_1_17.txt |
|  | 213-28 | X212669 | Axial | .053 OD | NA | 1 | 1 | AR_213-28_Axial_X212669_1_18.txt |
|  | 213-28 | X212669 | Axial | .053 OD | NA | 1 | 1 | AR_213-28_Axial_X212669_1_19.txt |
|  | 213-28 | X212669 | Axial | .053 OD | NA | 1 | 1 | AR_213-28_Axial_X212669_1_20.txt |
|  | 213-28 | X212669 | Axial | .053 OD | NA | 1 | 1 | AR_213-28_Axial_X212669_1_21.txt |
|  | 213-28 | X212669 | Axial | .053 OD | NA | 1 | 1 | AR_213-28_Axial_X212669_1_22.txt |
|  | 213-28 | X212669 | Axial | .053 OD | NA | 1 | 1 | AR_213-28_Axial_X212669_1_23.txt |
|  | 213-28 | X212669 | Axial | .053 OD | NA | 1 | 1 | AR_213-28_Axial_X212669_1_24.txt |
|  | 213-28 | X212669 | Axial | .053 OD | NA | 1 | 1 | AR_213-28_Axial_X212669_1_25.txt |
|  | 213-28 | X212669 | Axial | .053 OD | NA | 1 | 1 | AR_213-28_Axial_X212669_1_26.txt |
|  | 213-28 | X212669 | Axial | .053 OD | NA | 1 | 1 | AR_213-28_Axial_X212669_1_27.txt |
|  | 213-28 | X212669 | Axial | .053 OD | NA | 1 | 1 | AR_213-28_Axial_X212669_1_28.txt |
|  | 213-28 | X212669 | Axial | .053 OD | NA | 1 | 1 | AR_213-28_Axial_X212669_1_29.txt |
|  | 213-28 | X212669 | Axial | .053 OD | NA | 1 | 1 | AR_213-28_Axial_X212669_1_30.txt |
| Radial Static | 213-28 | X212669 | Radial | .053 OD | NA | 1 | 1 | AR_213-28_Radial_X212669_1_1.txt |
|  | 213-28 | X212669 | Radial | .053 OD | NA | 1 | 1 | AR_213-28_Radial_X212669_1_2.txt |
|  | 213-28 | X212669 | Radial | .053 OD | NA | 1 | 1 | AR_213-28_Radial_X212669_1_3.txt |
|  | 213-28 | X212669 | Radial | .053 OD | NA | 1 | 1 | AR_213-28_Radial_X212669_1_4.txt |
|  | 213-28 | X212669 | Radial | .053 OD | NA | 1 | 1 | AR_213-28_Radial_X212669_1_5.txt |
|  | 213-28 | X212669 | Radial | .053 OD | NA | 1 | 1 | AR_213-28_Radial_X212669_1_6.txt |
|  | 213-28 | X212669 | Radial | .053 OD | NA | 1 | 1 | AR_213-28_Radial_X212669_1_7.txt |
|  | 213-28 | X212669 | Radial | .053 OD | NA | 1 | 1 | AR_213-28_Radial_X212669_1_8.txt |
|  | 213-28 | X212669 | Radial | .053 OD | NA | 1 | 1 | AR_213-28_Radial_X212669_1_9.txt |
|  | 213-28 | X212669 | Radial | .053 OD | NA | 1 | 1 | AR_213-28_Radial_X212669_1_10.txt |
|  | 213-28 | X212669 | Radial | .053 OD | NA | 1 | 1 | AR_213-28_Radial_X212669_1_11.txt |

TABLE 1-continued

AXIAL AND RADIAL STATIC REFERENCES

| | | | | | | | | |
|---|---|---|---|---|---|---|---|---|
| 213-28 | X212669 | Radial | .053 OD | NA | 1 | 1 | AR_213-28_Radial_X212669_1_12.txt |
| 213-28 | X212669 | Radial | .053 OD | NA | 1 | 1 | AR_213-28_Radial_X212669_1_13.txt |
| 213-28 | X212669 | Radial | .053 OD | NA | 1 | 1 | AR_213-28_Radial_X212669_1_14.txt |
| 213-28 | X212669 | Radial | .053 OD | NA | 1 | 1 | AR_213-28_Radial_X212669_1_15.txt |
| 213-28 | X212669 | Radial | .053 OD | NA | 1 | 1 | AR_213-28_Radial_X212669_1_16.txt |
| 213-28 | X212669 | Radial | .053 OD | NA | 1 | 1 | AR_213-28_Radial_X212669_1_17.txt |
| 213-28 | X212669 | Radial | .053 OD | NA | 1 | 1 | AR_213-28_Radial_X212669_1_18.txt |
| 213-28 | X212669 | Radial | .053 OD | NA | 1 | 1 | AR_213-28_Radial_X212669_1_19.txt |
| 213-28 | X212669 | Radial | .053 OD | NA | 1 | 1 | AR_213-28_Radial_X212669_1_20.txt |
| 213-28 | X212669 | Radial | .053 OD | NA | 1 | 1 | AR_213-28_Radial_X212669_1_21.txt |
| 213-28 | X212669 | Radial | .053 OD | NA | 1 | 1 | AR_213-28_Radial_X212669_1_22.txt |
| 213-28 | X212669 | Radial | .053 OD | NA | 1 | 1 | AR_213-28_Radial_X212669_1_23.txt |
| 213-28 | X212669 | Radial | .053 OD | NA | 1 | 1 | AR_213-28_Radial_X212669_1_24.txt |
| 213-28 | X212669 | Radial | .053 OD | NA | 1 | 1 | AR_213-28_Radial_X212669_1_25.txt |
| 213-28 | X212669 | Radial | .053 OD | NA | 1 | 1 | AR_213-28_Radial_X212669_1_26.txt |
| 213-28 | X212669 | Radial | .053 OD | NA | 1 | 1 | AR_213-28_Radial_X212669_1_27.txt |
| 213-28 | X212669 | Radial | .053 OD | NA | 1 | 1 | AR_213-28_Radial_X212669_1_28.txt |
| 213-28 | X212669 | Radial | .053 OD | NA | 1 | 1 | AR_213-28_Radial_X212669_1_29.txt |
| 213-28 | X212669 | Radial | .053 OD | NA | 1 | 1 | AR_213-28_Radial_X212669_1_30.txt |

| | Research Report Number | Base Resistance (ohms) | Min Resistance (ohms) | Max Resistance (ohms) | Avg Resistance (ohms) | Net Resistance (ohms) | Std Dev Resistance (ohms) | Samples | Sample Rate (sec/sample) | Operator Initials |
|---|---|---|---|---|---|---|---|---|---|---|
| Axial Static | 213-28 | 0.003 | 0.056 | 0.089 | 0.071 | 0.068 | 0.009 | 33 | 4 | MM |
| | 213-28 | 0.003 | 0.05 | 0.084 | 0.069 | 0.066 | 0.0107 | 33 | 4 | MM |
| | 213-28 | 0.003 | 0.044 | 0.095 | 0.07 | 0.067 | 0.0126 | 33 | 4 | MM |
| | 213-28 | 0.003 | 0.045 | 0.084 | 0.068 | 0.065 | 0.0115 | 33 | 4 | MM |
| | 213-28 | 0.003 | 0.039 | 0.095 | 0.069 | 0.066 | 0.0123 | 33 | 4 | MM |
| | 213-28 | 0.003 | 0.05 | 0.084 | 0.072 | 0.069 | 0.009 | 33 | 4 | MM |
| | 213-28 | 0.003 | 0.045 | 0.089 | 0.067 | 0.064 | 0.011 | 33 | 4 | MM |
| | 213-28 | 0.003 | 0.039 | 0.084 | 0.069 | 0.066 | 0.0104 | 33 | 4 | MM |
| | 213-28 | 0.003 | 0.045 | 0.084 | 0.064 | 0.061 | 0.0108 | 33 | 4 | MM |
| | 213-28 | 0.003 | 0.056 | 0.101 | 0.071 | 0.068 | 0.0111 | 33 | 4 | MM |
| | 213-28 | 0.003 | 0.056 | 0.084 | 0.07 | 0.067 | 0.0102 | 33 | 4 | MM |
| | 213-28 | 0.003 | 0.045 | 0.084 | 0.063 | 0.06 | 0.0098 | 33 | 4 | MM |
| | 213-28 | 0.003 | 0.056 | 0.089 | 0.071 | 0.068 | 0.0097 | 33 | 4 | MM |
| | 213-28 | 0.003 | 0.045 | 0.084 | 0.064 | 0.061 | 0.0093 | 33 | 4 | MM |
| | 213-28 | 0.003 | 0.05 | 0.084 | 0.066 | 0.063 | 0.01 | 33 | 4 | MM |
| | 213-28 | 0.003 | 0.045 | 0.079 | 0.066 | 0.063 | 0.0085 | 33 | 4 | MM |
| | 213-28 | 0.003 | 0.05 | 0.084 | 0.066 | 0.063 | 0.0099 | 33 | 4 | MM |
| | 213-28 | 0.003 | 0.039 | 0.084 | 0.066 | 0.063 | 0.0101 | 33 | 4 | MM |
| | 213-28 | 0.003 | 0.056 | 0.079 | 0.067 | 0.064 | 0.007 | 33 | 4 | MM |
| | 213-28 | 0.003 | 0.056 | 0.079 | 0.067 | 0.064 | 0.0066 | 33 | 4 | MM |
| | 213-28 | 0.003 | 0.05 | 0.073 | 0.065 | 0.062 | 0.0059 | 33 | 4 | MM |
| | 213-28 | 0.003 | 0.056 | 0.079 | 0.067 | 0.064 | 0.0067 | 33 | 4 | MM |
| | 213-28 | 0.003 | 0.056 | 0.079 | 0.068 | 0.065 | 0.0067 | 33 | 4 | MM |
| | 213-28 | 0.003 | 0.061 | 0.084 | 0.088 | 0.065 | 0.0058 | 33 | 4 | MM |
| | 213-28 | 0.003 | 0.056 | 0.079 | 0.068 | 0.065 | 0.0073 | 33 | 4 | MM |
| | 213-28 | 0.003 | 0.061 | 0.079 | 0.068 | 0.065 | 0.0063 | 33 | 4 | MM |
| | 213-28 | 0.003 | 0.056 | 0.079 | 0.069 | 0.066 | 0.007 | 33 | 4 | MM |
| | 213-28 | 0.003 | 0.061 | 0.084 | 0.068 | 0.065 | 0.0061 | 33 | 4 | MM |
| | 213-28 | 0.003 | 0.056 | 0.079 | 0.068 | 0.065 | 0.0063 | 33 | 4 | MM |
| | 213-28 | 0.003 | 0.056 | 0.084 | 0.067 | 0.064 | 0.0065 | 33 | 4 | MM |
| | | | 1.536 | 2.518 | 2.032 | | | | | |
| | | AVERAGES> | 0.0512 | 0.0839 | 0.0677 | | | | | |
| Radial Static | 213-28 | 0.003 | 0.123 | 0.151 | 0.134 | 0.131 | 0.0068 | 33 | 4 | MM |
| | 213-28 | 0.003 | 0.117 | 0.14 | 0.13 | 0.127 | 0.0063 | 33 | 4 | MM |
| | 213-28 | 0.003 | 0.117 | 0.14 | 0.131 | 0.128 | 0.0061 | 33 | 4 | MM |
| | 213-28 | 0.003 | 0.106 | 0.129 | 0.121 | 0.118 | 0.006 | 33 | 4 | MM |
| | 213-28 | 0.003 | 0.101 | 0.129 | 0.117 | 0.114 | 0.0065 | 33 | 4 | MM |
| | 213-28 | 0.003 | 0.1 | 0.124 | 0.111 | 0.108 | 0.0074 | 33 | 4 | MM |
| | 213-28 | 0.003 | 0.095 | 0.118 | 0.11 | 0.107 | 0.0062 | 33 | 4 | MM |
| | 213-28 | 0.003 | 0.095 | 0.124 | 0.112 | 0.109 | 0.0069 | 33 | 4 | MM |
| | 213-28 | 0.003 | 0.1 | 0.118 | 0.11 | 0.107 | 0.0069 | 33 | 4 | MM |
| | 213-28 | 0.003 | 0.1 | 0.118 | 0.107 | 0.104 | 0.0066 | 33 | 4 | MM |
| | 213-28 | 0.003 | 0.1 | 0.118 | 0.107 | 0.104 | 0.0056 | 33 | 4 | MM |
| | 213-28 | 0.003 | 0.089 | 0.112 | 0.105 | 0.102 | 0.0062 | 33 | 4 | MM |
| | 213-28 | 0.003 | 0.089 | 0.118 | 0.102 | 0.099 | 0.0071 | 33 | 4 | MM |
| | 213-28 | 0.003 | 0.089 | 0.107 | 0.1 | 0.097 | 0.0061 | 33 | 4 | MM |
| | 213-28 | 0.003 | 0.089 | 0.112 | 0.101 | 0.098 | 0.0067 | 33 | 4 | MM |
| | 213-28 | 0.003 | 0.089 | 0.112 | 0.1 | 0.097 | 0.0073 | 33 | 4 | MM |
| | 213-28 | 0.003 | 0.089 | 0.112 | 0.1 | 0.097 | 0.0068 | 33 | 4 | MM |
| | 213-28 | 0.003 | 0.089 | 0.112 | 0.1 | 0.097 | 0.0067 | 33 | 4 | MM |
| | 213-28 | 0.003 | 0.089 | 0.112 | 0.101 | 0.098 | 0.0071 | 33 | 4 | MM |
| | 213-28 | 0.003 | 0.089 | 0.112 | 0.099 | 0.096 | 0.0069 | 33 | 4 | MM |
| | 213-28 | 0.003 | 0.089 | 0.112 | 0.101 | 0.098 | 0.0074 | 33 | 4 | MM |

TABLE 1-continued

AXIAL AND RADIAL STATIC REFERENCES

| | | | | | | | | | |
|---|---|---|---|---|---|---|---|---|---|
| 213-28 | 0.003 | 0.084 | 0.112 | 0.098 | 0.095 | 0.0067 | 33 | 4 | MM |
| 213-28 | 0.003 | 0.089 | 0.112 | 0.101 | 0.098 | 0.0069 | 33 | 4 | MM |
| 213-28 | 0.003 | 0.084 | 0.112 | 0.097 | 0.094 | 0.0072 | 33 | 4 | MM |
| 213-28 | 0.003 | 0.089 | 0.107 | 0.098 | 0.095 | 0.0061 | 33 | 4 | MM |
| 213-28 | 0.003 | 0.084 | 0.112 | 0.098 | 0.095 | 0.007 | 33 | 4 | MM |
| 213-28 | 0.003 | 0.089 | 0.107 | 0.097 | 0.094 | 0.0059 | 33 | 4 | MM |
| 213-28 | 0.003 | 0.089 | 0.107 | 0.098 | 0.095 | 0.0056 | 33 | 4 | MM |
| 213-28 | 0.003 | 0.084 | 0.107 | 0.094 | 0.091 | 0.0065 | 33 | 4 | MM |
| 213-28 | 0.003 | 0.069 | 0.112 | 0.099 | 0.096 | 0.007 | 33 | 4 | MM |
| | | 2.825 | 3.518 | 3.179 | | | | | |
| | AVERAGES> | 0.0941 | 0.1172 | | | 0.0105 | | | |

TABLE 2

AXIAL AND RADIAL DYNAMIC RESISTANCES

| | Research Report Number | Contact Part Number | Contact Item Number | Pin Part Number | Pin Item Code | Test Item | Header position | Filename |
|---|---|---|---|---|---|---|---|---|
| Axial Dynamic | 213-28 | X212669 | Axial | .053 OD | NA | 1 | 1 | SR_X212669_X221669_AXIAL_1_1_1.txt |
| | 213-28 | X212669 | Axial | .053 OD | NA | 1 | 1 | SR_X212669_X221669_AXIAL_1_1_2.txt |
| | 213-28 | X212669 | Axial | .053 OD | NA | 1 | 1 | SR_X212669_X221669_AXIAL_1_1_3.txt |
| | 213-28 | X212669 | Axial | .053 OD | NA | 1 | 1 | SR_X212669_X221669_AXIAL_1_1_4.txt |
| | 213-28 | X212669 | Axial | .053 OD | NA | 1 | 1 | SR_X212669_X221669_AXIAL_1_1_5.txt |
| | 213-28 | X212669 | Axial | .053 OD | NA | 1 | 1 | SR_X212669_X221669_AXIAL_1_1_6.txt |
| | 213-28 | X212669 | Axial | .053 OD | NA | 1 | 1 | SR_X212669_X221669_AXIAL_1_1_7.txt |
| | 213-28 | X212669 | Axial | .053 OD | NA | 1 | 1 | SR_X212669_X221669_AXIAL_1_1_8.txt |
| | 213-28 | X212669 | Axial | .053 OD | NA | 1 | 1 | SR_X212669_X221669_AXIAL_1_1_9.txt |
| | 213-28 | X212669 | Axial | .053 OD | NA | 1 | 1 | SR_X212669_X221669_AXIAL_1_1_10.txt |
| | 213-28 | X212669 | Axial | .053 OD | NA | 1 | 1 | SR_X212669_X221669_AXIAL_1_1_11.txt |
| | 213-28 | X212669 | Axial | .053 OD | NA | 1 | 1 | SR_X212669_X221669_AXIAL_1_1_12.txt |
| | 213-28 | X212669 | Axial | .053 OD | NA | 1 | 1 | SR_X212669_X221669_AXIAL_1_1_13.txt |
| | 213-28 | X212669 | Axial | .053 OD | NA | 1 | 1 | SR_X212669_X221669_AXIAL_1_1_14.txt |
| | 213-28 | X212669 | Axial | .053 OD | NA | 1 | 1 | SR_X212669_X221669_AXIAL_1_1_15.txt |
| | 213-28 | X212669 | Axial | .053 OD | NA | 1 | 1 | SR_X212669_X221669_AXIAL_1_1_16.txt |
| | 213-28 | X212669 | Axial | .053 OD | NA | 1 | 1 | SR_X212669_X221669_AXIAL_1_1_17.txt |
| | 213-28 | X212669 | Axial | .053 OD | NA | 1 | 1 | SR_X212669_X221669_AXIAL_1_1_18.txt |
| | 213-28 | X212669 | Axial | .053 OD | NA | 1 | 1 | SR_X212669_X221669_AXIAL_1_1_19.txt |
| | 213-28 | X212669 | Axial | .053 OD | NA | 1 | 1 | SR_X212669_X221669_AXIAL_1_1_20.txt |
| | 213-28 | X212669 | Axial | .053 OD | NA | 1 | 1 | SR_X212669_X221669_AXIAL_1_1_21.txt |
| | 213-28 | X212669 | Axial | .053 OD | NA | 1 | 1 | SR_X212669_X221669_AXIAL_1_1_22.txt |
| | 213-28 | X212669 | Axial | .053 OD | NA | 1 | 1 | SR_X212669_X221669_AXIAL_1_1_23.txt |
| | 213-28 | X212669 | Axial | .053 OD | NA | 1 | 1 | SR_X212669_X221669_AXIAL_1_1_24.txt |
| | 213-28 | X212669 | Axial | .053 OD | NA | 1 | 1 | SR_X212669_X221669_AXIAL_1_1_25.txt |
| | 213-28 | X212669 | Axial | .053 OD | NA | 1 | 1 | SR_X212669_X221669_AXIAL_1_1_26.txt |
| | 213-28 | X212669 | Axial | .053 OD | NA | 1 | 1 | SR_X212669_X221669_AXIAL_1_1_27.txt |
| | 213-28 | X212669 | Axial | .053 OD | NA | 1 | 1 | SR_X212669_X221669_AXIAL_1_1_28.txt |
| | 213-28 | X212669 | Axial | .053 OD | NA | 1 | 1 | SR_X212669_X221669_AXIAL_1_1_29.txt |
| | 213-28 | X212669 | Axial | .053 OD | NA | 1 | 1 | SR_X212669_X221669_AXIAL_1_1_30.txt |
| Radial Dynamic | 213-28 | X212669 | Radial | .053 OD | NA | 1 | 1 | SR_X212669_X221669_RADIAL_1_1_1.txt |
| | 213-28 | X212669 | Radial | .053 OD | NA | 1 | 1 | SR_X212669_X221669_RADIAL_1_1_2.txt |
| | 213-28 | X212669 | Radial | .053 OD | NA | 1 | 1 | SR_X212669_X221669_RADIAL_1_1_3.txt |
| | 213-28 | X212669 | Radial | .053 OD | NA | 1 | 1 | SR_X212669_X221669_RADIAL_1_1_4.txt |
| | 213-28 | X212669 | Radial | .053 OD | NA | 1 | 1 | SR_X212669_X221669_RADIAL_1_1_5.txt |
| | 213-28 | X212669 | Radial | .053 OD | NA | 1 | 1 | SR_X212669_X221669_RADIAL_1_1_6.txt |
| | 213-28 | X212669 | Radial | .053 OD | NA | 1 | 1 | SR_X212669_X221669_RADIAL_1_1_7.txt |
| | 213-28 | X212669 | Radial | .053 OD | NA | 1 | 1 | SR_X212669_X221669_RADIAL_1_1_8.txt |
| | 213-28 | X212669 | Radial | .053 OD | NA | 1 | 1 | SR_X212669_X221669_RADIAL_1_1_9.txt |
| | 213-28 | X212669 | Radial | .053 OD | NA | 1 | 1 | SR_X212669_X221669_RADIAL_1_1_10.T) |
| | 213-28 | X212669 | Radial | .053 OD | NA | 1 | 1 | SR_X212669_X221669_RADIAL_1_1_11.txt |
| | 213-28 | X212669 | Radial | .053 OD | NA | 1 | 1 | SR_X212669_X221669_RADIAL_1_1_12.txt |
| | 213-28 | X212669 | Radial | .053 OD | NA | 1 | 1 | SR_X212669_X221669_RADIAL_1_1_13.txt |
| | 213-28 | X212669 | Radial | .053 OD | NA | 1 | 1 | SR_X212669_X221669_RADIAL_1_1_14.txt |
| | 213-28 | X212669 | Radial | .053 OD | NA | 1 | 1 | SR_X212669_X221669_RADIAL_1_1_15.txt |
| | 213-28 | X212669 | Radial | .053 OD | NA | 1 | 1 | SR_X212669_X221669_RADIAL_1_1_16.txt |
| | 213-28 | X212669 | Radial | .053 OD | NA | 1 | 1 | SR_X212669_X221669_RADIAL_1_1_17.txt |
| | 213-28 | X212669 | Radial | .053 OD | NA | 1 | 1 | SR_X212669_X221669_RADIAL_1_1_18.txt |
| | 213-28 | X212669 | Radial | .053 OD | NA | 1 | 1 | SR_X212669_X221669_RADIAL_1_1_19.txt |
| | 213-28 | X212669 | Radial | .053 OD | NA | 1 | 1 | SR_X212669_X221669_RADIAL_1_1_20.txt |
| | 213-28 | X212669 | Radial | .053 OD | NA | 1 | 1 | SR_X212669_X221669_RADIAL_1_1_21.txt |
| | 213-28 | X212669 | Radial | .053 OD | NA | 1 | 1 | SR_X212669_X221669_RADIAL_1_1_22.txt |
| | 213-28 | X212669 | Radial | .053 OD | NA | 1 | 1 | SR_X212669_X221669_RADIAL_1_1_23.txt |
| | 213-28 | X212669 | Radial | .053 OD | NA | 1 | 1 | SR_X212669_X221669_RADIAL_1_1_24.txt |

TABLE 2-continued

AXIAL AND RADIAL DYNAMIC RESISTANCES

| | 213-28 | X212669 | Radial | .053 OD | NA | 1 | 1 | SR_X212669_X221669_RADIAL_1_1_25.txt |
|---|---|---|---|---|---|---|---|---|
| | 213-28 | X212669 | Radial | .053 OD | NA | 1 | 1 | SR_X212669_X221669_RADIAL_1_1_26.txt |
| | 213-28 | X212669 | Radial | .053 OD | NA | 1 | 1 | SR_X212669_X221669_RADIAL_1_1_27.txt |
| | 213-28 | X212669 | Radial | .053 OD | NA | 1 | 1 | SR_X212669_X221669_RADIAL_1_1_28.txt |
| | 213-28 | X212669 | Radial | .053 OD | NA | 1 | 1 | SR_X212669_X221669_RADIAL_1_1_29.txt |
| | 213-28 | X212669 | Radial | .053 OD | NA | 1 | 1 | SR_X212669_X221669_RADIAL_1_1_30.txt |

| | Research Report Number | Base Resistance (ohms) | Min Resistance (ohms) | Max Resistance (ohms) | Avg Resistance (ohms) | Net Resistance (ohms) | Std Dev Resistance (ohms) | Samples | Sample Rate (sec/sample) | Operator Initials |
|---|---|---|---|---|---|---|---|---|---|---|
| Axial Dynamic | 213-28 | 0.023 | 0.032 | 0.044 | 0.04 | 0.017 | 0.0034 | 33 | 1 | MM |
| | 213-28 | 0.023 | 0.04 | 0.043 | 0.041 | 0.018 | 0.001 | 33 | 1 | MM |
| | 213-28 | 0.023 | 0.036 | 0.04 | 0.038 | 0.015 | 0.0012 | 33 | 1 | MM |
| | 213-28 | 0.023 | 0.039 | 0.045 | 0.042 | 0.019 | 0.0015 | 33 | 1 | MM |
| | 213-28 | 0.023 | 0.043 | 0.048 | 0.045 | 0.022 | 0.0014 | 33 | 1 | MM |
| | 213-28 | 0.023 | 0.041 | 0.049 | 0.044 | 0.021 | 0.0019 | 33 | 1 | MM |
| | 213-28 | 0.023 | 0.04 | 0.043 | 0.042 | 0.019 | 0.0007 | 33 | 1 | MM |
| | 213-28 | 0.023 | 0.039 | 0.042 | 0.04 | 0.017 | 0.0007 | 33 | 1 | MM |
| | 213-28 | 0.023 | 0.037 | 0.049 | 0.045 | 0.022 | 0.0033 | 33 | 1 | MM |
| | 213-28 | 0.023 | 0.046 | 0.051 | 0.049 | 0.026 | 0.0014 | 33 | 1 | MM |
| | 213-28 | 0.023 | 0.048 | 0.052 | 0.05 | 0.027 | 0.0011 | 33 | 1 | MM |
| | 213-28 | 0.023 | 0.048 | 0.054 | 0.051 | 0.028 | 0.0015 | 33 | 1 | MM |
| | 213-28 | 0.023 | 0.049 | 0.057 | 0.054 | 0.031 | 0.0022 | 33 | 1 | MM |
| | 213-28 | 0.023 | 0.048 | 0.054 | 0.051 | 0.028 | 0.0021 | 33 | 1 | MM |
| | 213-28 | 0.023 | 0.046 | 0.054 | 0.049 | 0.026 | 0.002 | 33 | 1 | MM |
| | 213-28 | 0.023 | 0.045 | 0.053 | 0.049 | 0.026 | 0.0022 | 33 | 1 | MM |
| | 213-28 | 0.023 | 0.043 | 0.051 | 0.047 | 0.024 | 0.0023 | 33 | 1 | MM |
| | 213-28 | 0.023 | 0.04 | 0.048 | 0.044 | 0.021 | 0.002 | 33 | 1 | MM |
| | 213-28 | 0.023 | 0.039 | 0.046 | 0.043 | 0.02 | 0.0018 | 33 | 1 | MM |
| | 213-28 | 0.023 | 0.039 | 0.047 | 0.042 | 0.019 | 0.002 | 33 | 1 | MM |
| | 213-28 | 0.023 | 0.037 | 0.043 | 0.04 | 0.017 | 0.0016 | 33 | 1 | MM |
| | 213-28 | 0.023 | 0.037 | 0.043 | 0.04 | 0.017 | 0.0017 | 33 | 1 | MM |
| | 213-28 | 0.023 | 0.038 | 0.043 | 0.041 | 0.018 | 0.0015 | 33 | 1 | MM |
| | 213-28 | 0.023 | 0.038 | 0.047 | 0.042 | 0.019 | 0.0021 | 33 | 1 | MM |
| | 213-28 | 0.023 | 0.04 | 0.045 | 0.043 | 0.02 | 0.0014 | 33 | 1 | MM |
| | 213-28 | 0.023 | 0.039 | 0.044 | 0.041 | 0.018 | 0.0015 | 33 | 1 | MM |
| | 213-28 | 0.023 | 0.037 | 0.044 | 0.04 | 0.017 | 0.0018 | 33 | 1 | MM |
| | 213-28 | 0.023 | 0.037 | 0.042 | 0.039 | 0.016 | 0.0016 | 33 | 1 | MM |
| | 213-28 | 0.023 | 0.038 | 0.046 | 0.042 | 0.019 | 0.0022 | 33 | 1 | MM |
| | 213-28 | 0.023 | 0.032 | 0.042 | 0.038 | 0.015 | 0.0024 | 33 | 1 | MM |
| | | | 1.209 | 1.409 | 1.312 | | | | | |
| | AVERAGES> | | 0.0403 | 0.0469 | 0.0437 | | | | | |
| Radial Dynamic | 213-28 | 0.023 | 0.065 | 0.105 | 0.093 | 0.07 | 0.0113 | 33 | 1 | MM |
| | 213-28 | 0.023 | 0.069 | 0.089 | 0.079 | 0.056 | 0.0065 | 33 | 1 | MM |
| | 213-28 | 0.023 | 0.058 | 0.069 | 0.064 | 0.041 | 0.0036 | 33 | 1 | MM |
| | 213-28 | 0.023 | 0.05 | 0.058 | 0.054 | 0.031 | 0.0023 | 33 | 1 | MM |
| | 213-28 | 0.023 | 0.048 | 0.05 | 0.048 | 0.025 | 0.0015 | 33 | 1 | MM |
| | 213-28 | 0.023 | 0.044 | 0.046 | 0.045 | 0.022 | 0.0007 | 33 | 1 | MM |
| | 213-28 | 0.023 | 0.039 | 0.042 | 0.041 | 0.018 | 0.0008 | 33 | 1 | MM |
| | 213-28 | 0.023 | 0.039 | 0.041 | 0.04 | 0.017 | 0.0006 | 33 | 1 | MM |
| | 213-28 | 0.023 | 0.04 | 0.041 | 0.04 | 0.017 | 0.0005 | 33 | 1 | MM |
| | 213-28 | 0.023 | 0.039 | 0.052 | 0.043 | 0.02 | 0.0034 | 33 | 1 | MM |
| | 213-28 | 0.023 | 0.053 | 0.057 | 0.056 | 0.033 | 0.0011 | 33 | 1 | MM |
| | 213-28 | 0.023 | 0.05 | 0.055 | 0.052 | 0.029 | 0.001 | 33 | 1 | MM |
| | 213-28 | 0.023 | 0.05 | 0.056 | 0.053 | 0.03 | 0.0015 | 33 | 1 | MM |
| | 213-28 | 0.023 | 0.058 | 0.064 | 0.08 | 0.037 | 0.0024 | 33 | 1 | MM |
| | 213-28 | 0.023 | 0.053 | 0.057 | 0.055 | 0.032 | 0.0012 | 33 | 1 | MM |
| | 213-28 | 0.023 | 0.05 | 0.054 | 0.051 | 0.028 | 0.0011 | 33 | 1 | MM |
| | 213-28 | 0.023 | 0.048 | 0.05 | 0.049 | 0.026 | 0.0005 | 33 | 1 | MM |
| | 213-28 | 0.023 | 0.049 | 0.051 | 0.05 | 0.027 | 0.0006 | 33 | 1 | MM |
| | 213-28 | 0.023 | 0.052 | 0.055 | 0.053 | 0.03 | 0.0011 | 33 | 1 | MM |
| | 213-28 | 0.023 | 0.059 | 0.108 | 0.07 | 0.047 | 0.0111 | 33 | 1 | MM |
| | 213-28 | 0.023 | 0.047 | 0.049 | 0.048 | 0.025 | 0.0006 | 33 | 1 | MM |
| | 213-28 | 0.023 | 0.044 | 0.049 | 0.047 | 0.024 | 0.0009 | 33 | 1 | MM |
| | 213-28 | 0.023 | 0.048 | 0.047 | 0.048 | 0.023 | 0.0005 | 33 | 1 | MM |
| | 213-28 | 0.023 | 0.045 | 0.046 | 0.048 | 0.023 | 0.0003 | 33 | 1 | MM |
| | 213-28 | 0.023 | 0.045 | 0.046 | 0.046 | 0.023 | 0.0005 | 33 | 1 | MM |
| | 213-28 | 0.023 | 0.045 | 0.047 | 0.046 | 0.023 | 0.0006 | 33 | 1 | MM |
| | 213-28 | 0.023 | 0.045 | 0.046 | 0.045 | 0.022 | 0.0004 | 33 | 1 | MM |
| | 213-28 | 0.023 | 0.045 | 0.046 | 0.045 | 0.022 | 0.0005 | 33 | 1 | MM |
| | 213-28 | 0.023 | 0.075 | 0.099 | 0.083 | 0.08 | 0.0058 | 33 | 1 | MM |
| | 213-28 | 0.023 | 0.07 | 0.076 | 0.072 | 0.049 | 0.0016 | 33 | 1 | MM |
| | | | 1.516 | 1.751 | 1.62 | | | | | |
| | AVERAGES> | | 0.0505 | 0.0583 | 0.054 | | | | | |

What is claimed is:

1. A medically implantable electrical connector comprising:
   a housing having a bore with an internal groove therein;
   a pin sized for insertion into the housing bore; and
   a film removing axial canted coil spring, having coils of different shape, disposed in the housing groove, dynamic loading of the spring in the groove by said pin causing scraping of film from groove and pin surfaces to provide lowered electrical resistance and resistance variability therebetween.

2. The connector according to claim 1 wherein said film removing spring includes both axial elliptical and axial round coils, the elliptical and round coils being offset radially from one another.

3. The connector according to claim 2 wherein a coil height of the elliptical coils is greater than a coil height of the round coils.

4. The connector according to claim 2 wherein a coil height of the round coils is greater than a coil height of the elliptical coils.

5. The connector according to claim 1 wherein the film removing spring comprises round coils of different coil heights.

6. The connector according to claim 1 wherein said pin includes an external groove for capturing the spring in order to removably latch said spring within the housing bore.

7. The connector according to claim 1 wherein the housing groove has a V-bottom.

8. The connector according to claim 1 wherein the housing groove has a flat bottom.

9. The connector according to claim 1 wherein the housing groove has a tapered bottom.

10. A medically implantable electrical connector comprising:
    a housing having a bore with an internal groove therein;
    a pin sized for insertion into the housing bore; and
    a film removing axial canted coil spring, having elliptical coils of different coil heights, disposed in the housing groove, dynamic loading of the spring in the groove by said pin causing scraping of film from groove and pin surfaces to provide lowered electrical resistance and resistance variability therebetween.

11. The connector according to claim 10 wherein the coils of different coil height are offset radially and axially from one another.

12. The connector according to claim 10 wherein the coils of different coil height are offset radially from one another.

* * * * *